(12) United States Patent
Igarashi

(10) Patent No.: US 11,938,256 B2
(45) Date of Patent: Mar. 26, 2024

(54) BLOOD COMPONENT COLLECTION CASSETTE HAVING FLOW CONTROL FEATURES FOR PRESSURE SENSING

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 840 days.

(21) Appl. No.: 16/621,191

(22) PCT Filed: Apr. 20, 2018

(86) PCT No.: PCT/JP2018/016305
§ 371 (c)(1),
(2) Date: Dec. 10, 2019

(87) PCT Pub. No.: WO2018/230156
PCT Pub. Date: Dec. 20, 2018

(65) Prior Publication Data
US 2020/0222614 A1    Jul. 16, 2020

(30) Foreign Application Priority Data
Jun. 16, 2017 (JP) ................................ 2017-118854

(51) Int. Cl.
*A61M 1/30* (2006.01)
*A61M 1/36* (2006.01)

(52) U.S. Cl.
CPC ...... *A61M 1/302* (2014.02); *A61M 1/362261* (2022.05); *A61M 1/362264* (2022.05);
(Continued)

(58) Field of Classification Search
None
See application file for complete search history.

(56) References Cited

U.S. PATENT DOCUMENTS 5,868,696 A * 2/1999 Giesler ............... A61M 1/3696
604/6.12
6,491,656 B1 * 12/2002 Morris ................. A61M 1/303
210/321.62
(Continued)

FOREIGN PATENT DOCUMENTS

EP 3228341 A1 10/2017
JP 2002-513321 5/2002
(Continued)

OTHER PUBLICATIONS

Official Action (with English translation) for Japan Patent Application No. 2019-565960, dated Dec. 21, 2021, 12 pages.

*Primary Examiner* — Jonathan M Peo
(74) *Attorney, Agent, or Firm* — Sheridan Ross P.C.

(57) ABSTRACT

Provided is a blood component collection cassette capable of measuring a circuit internal pressure using a simple and economical configuration. A blood component collection cassette includes an inflow line for sending blood or a blood component collected from a donor to a centrifugal separator, a return line for returning a predetermined blood component to the donor, and a line forming member forming one of the inflow line and the return line and having a load detection soft portion made of a soft material.

20 Claims, 13 Drawing Sheets

(52) U.S. Cl.
CPC ..... *A61M 1/3693* (2013.01); *A61M 2205/125* (2013.01); *A61M 2205/70* (2013.01); *A61M 2205/7545* (2013.01)

(56) References Cited

U.S. PATENT DOCUMENTS

| | | | |
|---|---|---|---|
| 2002/0077582 A1* | 6/2002 | Mehdi | A61M 1/3693 604/6.11 |
| 2013/0164854 A1* | 6/2013 | Wang | B01L 3/502753 436/63 |

FOREIGN PATENT DOCUMENTS

| | | | | |
|---|---|---|---|---|
| JP | 2002-527212 | 8/2002 | | |
| JP | 3117223 | 1/2006 | | |
| JP | 2010-538803 | 12/2010 | | |
| WO | WO-2004037375 A1 * | 5/2004 | .......... | A61M 1/3633 |
| WO | 2004061399 A2 | 4/2007 | | |
| WO | 1996040322 A2 | 5/2007 | | |
| WO | WO 2017/038624 | 3/2017 | | |

\* cited by examiner

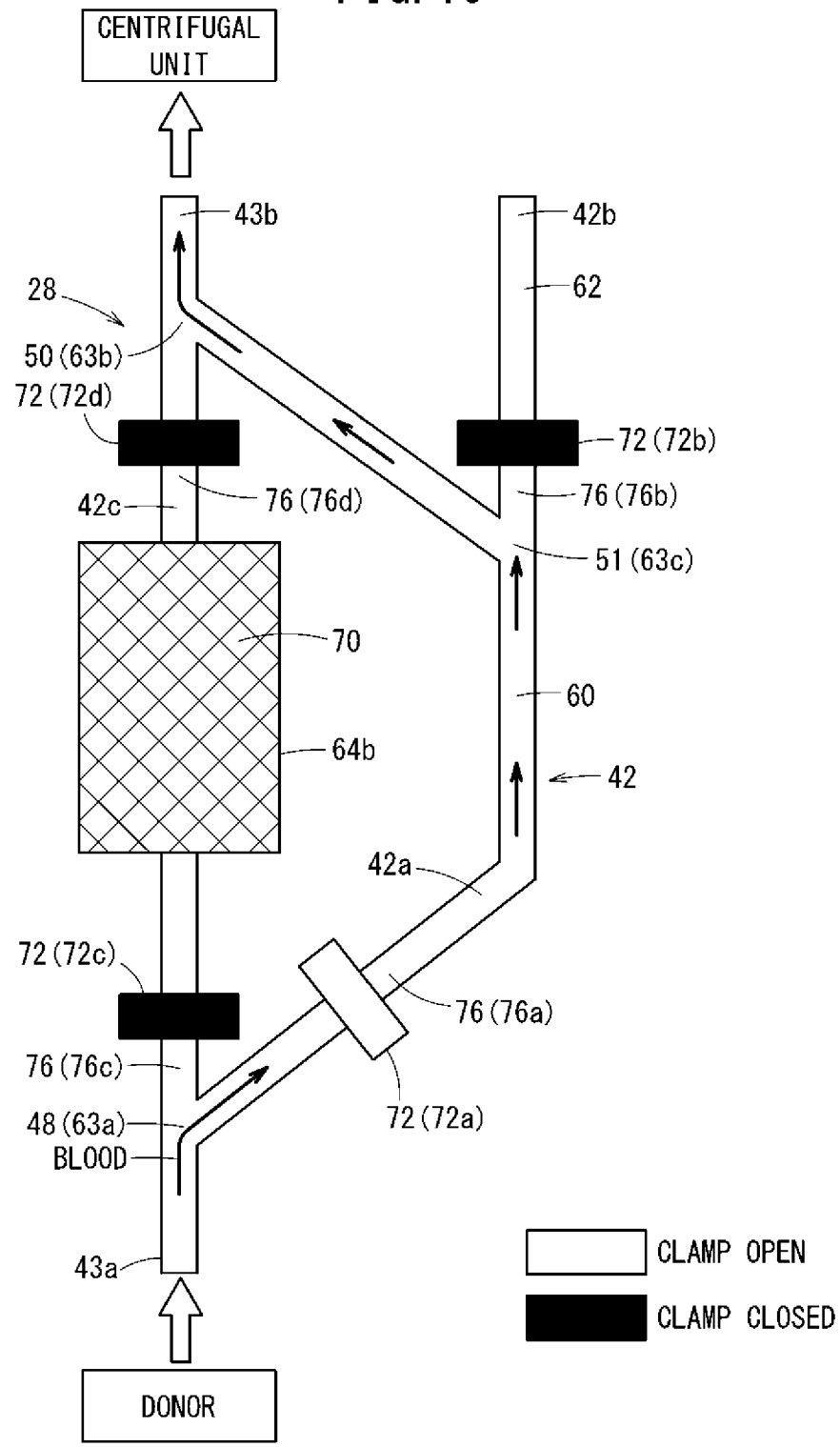

BLOOD COMPONENT COLLECTION CASSETTE HAVING FLOW CONTROL FEATURES FOR PRESSURE SENSING

TECHNICAL FIELD

The present invention relates to a blood component collection cassette.

BACKGROUND ART

In blood donation of recent years, besides whole blood collection for collecting whole blood from a donor, component collection (apheresis) which is a light burden on a body of the donor has been carried out. Component collection is a blood collection method that uses a blood component collection system (apheresis system), collects only specific blood components from whole blood, and returns remaining components into the body of the donor again.

PTL 1 discloses a blood component collection system that collects platelets by centrifuging whole blood taken out of a donor. This blood component collection system includes a blood collection circuit set forming a circuit through which blood or blood components to be treated flow, and a centrifugal separator (blood component separation device) to which the blood collection circuit set is attached.

The blood collection circuit set includes a blood collection line having a blood collection needle, a strip-like channel (separator) into which whole blood is introduced, a plurality of bags for accommodating a blood component, etc., and a cassette connected thereto through a plurality of tubes. A plurality of flow paths including a line for introducing blood from the donor, a line for transferring blood components to a bag, a blood return line for returning blood components not collected to the donor, etc., are formed in the cassette. During use, the cassette is attached to an attaching portion provided in the blood component separation device.

CITATION LIST

Patent Literature

[PTL 1]
JP 2013-514863 A

SUMMARY OF INVENTION

Technical Problem

The cassette of the conventional blood component collection system is a molded product of a hard resin produced by injection molding, and thus has a problem that a structure is complicated and the manufacturing cost is high. In addition, in the blood component collection system, it is necessary to measure and monitor a pressure (circuit internal pressure) in the blood collection circuit in order to verify whether the blood component separation device properly operates.

The present invention has been made in view of the above problems, and it is an object thereof to provide a blood component collection cassette capable of measuring a circuit internal pressure using a simple and economical configuration.

Solution to Problem

To achieve the above-mentioned object, the present invention is a blood component collection cassette configured to be attachable to a blood component separation device, including an inflow line for sending blood or a blood component collected from a donor to the blood component separation device, a return line for returning a predetermined blood component to the donor, and a line forming member forming one of the inflow line and the return line and having a load detection soft portion made of a soft material.

In the blood component collection cassette of the present invention configured as described above, at least a part is made of a soft material. Thus, the blood component collection cassette may be manufactured at low cost when compared to a conventional cassette made of a hard material and manufactured by injection molding. In addition, since the load detection soft portion made of the soft material is provided, it is possible to measure a circuit internal pressure.

The blood component separation device may include a load detector, and the load detection soft portion may correspond to a pressure-receiving portion to be pressed by the load detector in an attached state where the blood component collection cassette is attached to the blood component separation device.

The inflow line and the return line may be provided inside a cassette body having a sheet shape made of a soft material.

The inflow line and the return line may be provided inside a cassette body entirely made of a single soft material.

The load detector of the blood component separation device may include a first load detector and a second load detector, the blood component collection cassette may include a cavity through which blood and blood components do not flow when the blood component separation device is in operation, and a cavity forming member forming the cavity, the pressure-receiving portion may comprise a first pressure-receiving portion, and the cavity forming member includes a second pressure-receiving portion made of a soft material and pressed by the second load detector in the attached state.

According to this configuration, it is possible to accurately measure a circuit internal pressure (negative pressure and positive pressure) based on the load detected by the first load detector and the load detected by the second load detector.

The cavity may communicate with one of the inflow line and the return line via a coupling portion.

According to this configuration, it is possible to easily form the cavity.

An action portion on which a flow path opening/closing mechanism included in the blood component separation device acts may be provided between the coupling portion and the second pressure-receiving portion.

According to this configuration, it is possible to easily construct the cavity not communicating with the inflow line and the return line at the time of operation of the blood component separation device.

One of the inflow line and the return line may have a branch portion that branches one fluid passage into a plurality of fluid passages or a merging portion that merges a plurality of fluid passages into one fluid passage, and the branch portion or the merging portion may be configured such that a change in flow direction of a fluid in the branch portion or the merging portion corresponds to an obtuse angle.

According to this configuration, it is possible to reduce damage to blood when blood flows through the branch portion or the merging portion.

One of the inflow line and the return line may have a branch portion that branches one fluid passage into a plurality of fluid passages or a merging portion that merges a plurality of fluid passages into one fluid passage, and a flow path diameter of the branch portion or the merging portion may be smaller than a flow path diameter of a line adjacent to the branch portion or the merging portion.

According to this configuration, the flow path of the branch portion or the merging portion may be inhibited from being crushed.

One of the inflow line and the return line may have a branch portion that branches one fluid passage into a plurality of fluid passages or a merging portion that merges a plurality of fluid passages into one fluid passage, and the branch portion or the merging portion may have a protrusion partially protruding from an inner wall into a flow path.

According to this configuration, the flow path of the branch portion or the merging portion may be inhibited from being crushed.

A first port member and a second port member made of a hard material may be provided at an outer peripheral edge of the blood component collection cassette.

According to this configuration, the blood component collection cassette can be accurately attached to a predetermined position of the blood component separation device.

The first port member and the second port member may be provided at asymmetric positions with respect to each other.

According to this configuration, the blood component collection cassette may be attached to the blood component separation device in an accurate orientation.

The inflow line and the return line may be provided in a cassette body made of a soft material, the inflow line and the return line may have a first fluid passage in which the first pressure-receiving portion is provided and a second fluid passage provided in parallel with the first fluid passage, and a notch may be provided between the first fluid passage and the second fluid passage in the cassette body.

According to this configuration, it is possible to prevent an influence of deformation in the second fluid passage on the first fluid passage in which the pressure-receiving portion is provided.

The inflow line and the return line may be provided in a cassette body having a first sheet and a second sheet made of a soft material, the first sheet and the second sheet may be overlapped in a thickness direction and coupled to each other by welding, a seal portion corresponding to a welding position may be formed along the inflow line and the return line, and a seal width of the seal portion formed on both sides of the pressure-receiving portion may be larger than a seal width of the seal portion formed on both sides of a flow path adjacent to the pressure-receiving portion.

According to this configuration, a non-sealed portion in the cassette body may be prevented from coming into contact with the load detector.

The blood component collection cassette may be provided on a line for transferring whole blood collected from the donor to the blood component separation device, the whole blood may be introduced to the inflow line of the blood component collection cassette from a first inlet provided in the blood component collection cassette, branching into the inflow line and a first branch line may occur at a first branch portion provided at a downstream of the first inlet, the inflow line and the first branch line may be merged via a first merging portion, the whole blood may flow out toward the blood component separation device from a first outlet provided in the blood component collection cassette via the first branch portion and the first merging portion when the whole blood flows through the inflow line, at least one blood component among predetermined blood components separated by the blood component separation device may be introduced to the return line via a second inlet provided in the blood component collection cassette, branching into the return line and a second branch line may occur at a second branch portion provided at a downstream of the second inlet, the return line and the second branch line may be merged via a second merging portion, and the at least one blood component may flow out toward the donor from a second outlet provided in the blood component collection cassette via the second branch portion and the second merging portion when the at least one blood component flows through the return line.

In addition, the present invention is a blood component collection cassette configured to be attachable to a blood component separation device having a load detector, including a cassette body having a sheet shape made of a soft material, a plurality of fluid passages provided in the cassette body to send whole blood or a predetermined blood component collected from a donor, a branch portion provided in the cassette body to branch the plurality of fluid passages, a first port provided in one of the plurality of fluid passages and connected to a blood collecting portion for collecting blood from the donor, a second port provided in one of the plurality of fluid passages and connected to a processing unit that separates the whole blood or the predetermined blood component, and a pressure-receiving portion provided in a passage forming portion that forms one of the plurality of fluid passages and pressed by the load detector in an attached state in which the blood component collection cassette is attached to the blood component separation device.

Advantageous Effects of Invention

According to a blood component collection cassette of the present invention, it is possible to measure a circuit internal pressure using a simple and economical configuration.

BRIEF DESCRIPTION OF DRAWINGS

FIG. 10 is a fifth explanatory diagram for description of an operation of the clamp.

DESCRIPTION OF EMBODIMENTS

Hereinafter, a blood component collection cassette according to the present invention will be described with reference to accompanying drawings using preferred embodiments.

Figure 1:
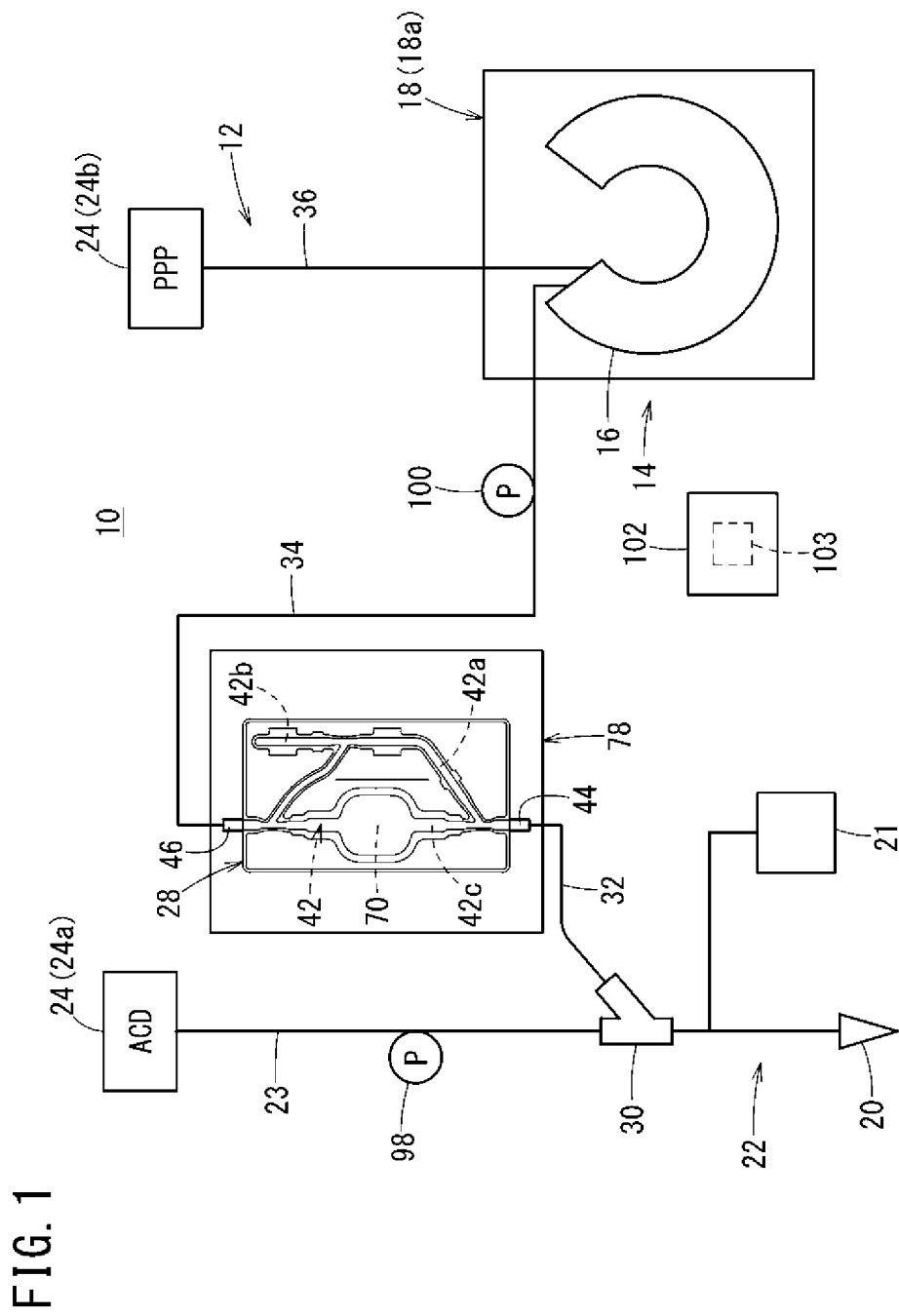
FIG. 1 is a schematic view of a blood component collection system according to an embodiment of the present invention.

In FIG. 1, a blood component collection system 10 is configured as a blood apheresis system that continuously extracts blood (whole blood) from a donor and centrifugally separates the blood outside a body, thereby collecting a specific blood component (plasma (platelet poor plasma: PPP) in the present embodiment) and returns remaining blood components to the donor.

First, a description will be given of an outline of the blood component collection system 10 illustrated in FIG. 1. The blood component collection system 10 includes a blood collection circuit set 12 for storing and allowing a blood component to flow therethrough, and a centrifugal separator 14 (blood component separation device) for applying a centrifugal force to the blood collection circuit set 12. The blood collection circuit set 12 has a blood processing unit 16 to which whole blood extracted from the donor is introduced and which centrifugally separates the whole blood into a plurality of blood components. The centrifugal separator 14 includes a centrifugal unit 18 having a rotor 18a for applying a centrifugal force to the blood processing unit 16. The blood processing unit 16 can be attached to the centrifugal unit 18.

The blood collection circuit set 12 is disposed of after being used once for contamination prevention and hygiene. The blood collection circuit set 12 includes a blood collection/blood return portion 22 having a blood collection needle 20 and an initial flow blood collection bag 21, the blood processing unit 16, a plurality of bags 24, and a blood component collection cassette 28 (hereinafter abbreviated to "cassette 28") connected to these elements via tubes. The plurality of bags 24 include an ACD solution bag 24a accommodating an ACD solution corresponding to an anticoagulant and a PPP bag 24b for storing plasma (platelet poor plasma).

The blood collection/blood return portion 22 is connected to the ACD solution bag 24a and the cassette 28 via a tube connector 30. The ACD solution bag 24a is connected to the tube connector 30 via the ACD solution transfer tube 23.

The cassette 28 is connected to the blood collection/blood return portion 22 via the donor-side tube 32 and is connected to the blood processing unit 16 via a processing unit-side tube 34. The blood processing unit 16 is attached to the centrifugal unit 18 (rotor 18a) of the centrifugal separator 14, and is configured in a container shape so that blood can be introduced, flowed, and flowed out. The PPP bag 24b is connected to the blood processing unit 16 via the PPP transfer tube 36.

Figure 2:
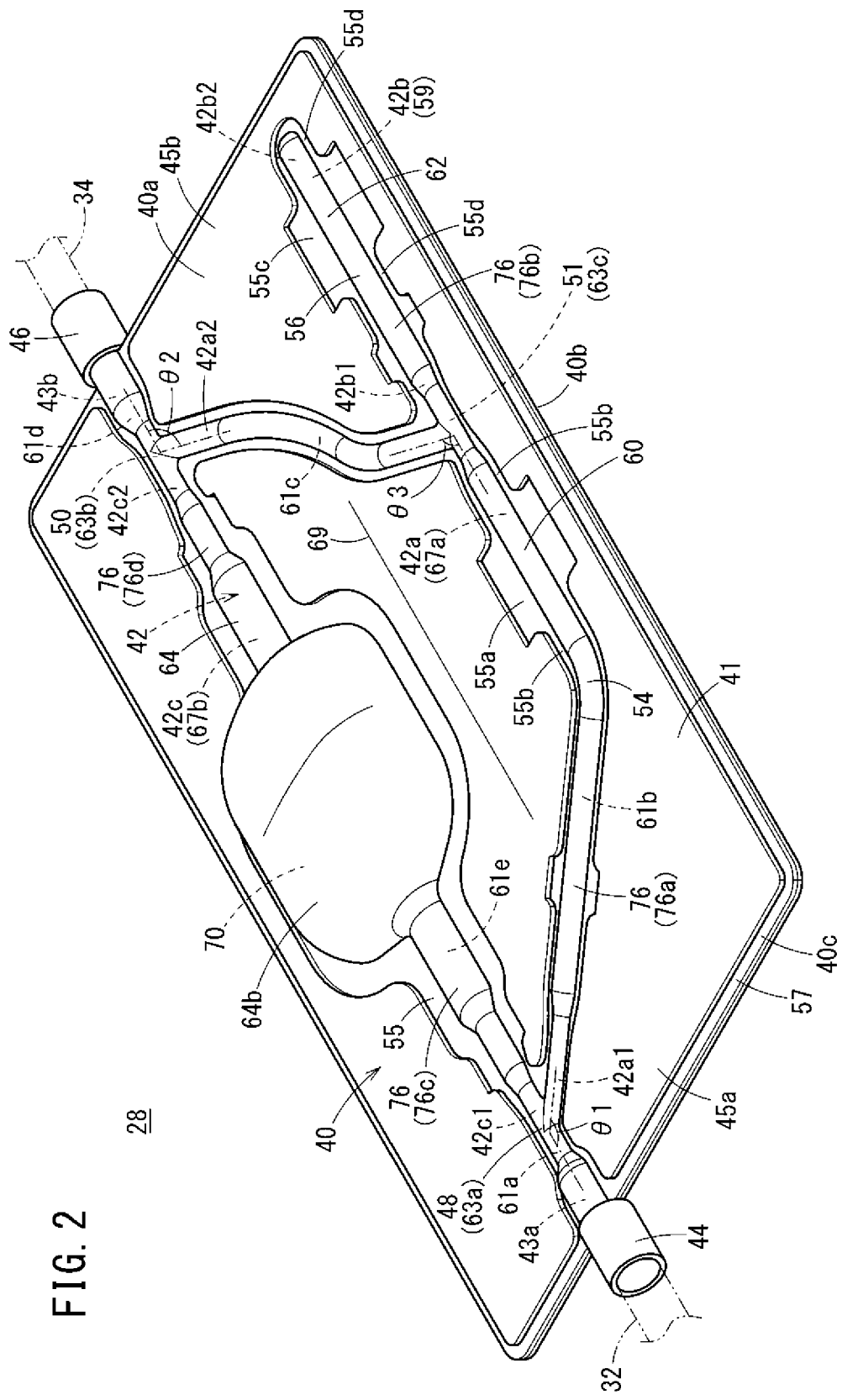
FIG. 2 is a perspective view of a blood component collection cassette.

In FIG. 2, the cassette 28 includes a cassette body 40 in which a flow path 42 is formed. The cassette body 40 is formed in a rectangular shape in a plan view. The cassette body 40 is made of a soft material. The same material is used over the entirety of the cassette body 40 as the soft material contained in the cassette body 40. The cassette body 40 may be made of a plurality of different materials. Specifically, the cassette body 40 has a first sheet 40a and a second sheet 40b made of a soft material. The first sheet 40a and the second sheet 40b are stacked in a thickness direction and joined to each other.

Examples of the soft material contained in the first sheet 40a and the second sheet 40b include vinyl chloride, polyolefin, polyurethane, etc. Examples of a plasticizer of vinyl chloride include diisononylcyclohexane-1,2-dicarboxylate, bis-2-ethylhexyl phthalate, etc.

The flow path 42 is formed between the first sheet 40a and the second sheet 40b. In the present embodiment, joining means between the first sheet 40a and the second sheet 40b corresponds to welding (high frequency welding, heat welding, etc.). The first sheet 40a and the second sheet 40b may be joined by other joining means (adhesion, etc.). In addition, a first port member 44 and a second port member 46 which are made of a hard material (for example, polypropylene, polycarbonate, etc.) are provided at an outer peripheral edge 40c of the cassette body 40.

The first port member 44 is provided at a first end 45a which is one longitudinal end of the rectangular cassette body 40 and is connected to a first port 43a provided at one end side of the flow path 42. The second port member 46 is provided at a second end 45b which is the other longitudinal end of the cassette body 40, and is connected to a second port 43b provided on the other end side of the flow path 42. The donor-side tube 32 and the processing unit-side tube 34 are connected to the port members 44 and 46, respectively.

In the present embodiment, the first port member 44 and the second port member 46 are arranged on the same straight line along a major axis direction of the rectangular cassette body 40. It should be noted that the first port member 44 and the second port member 46 may not be arranged on the same straight line. In other words, the first port member 44 and the second port member 46 may be provided at asymmetric positions with respect to a center line in a minor axis direction of the rectangular cassette body 40. According to this configuration, in a state in which the cassette 28 is upside down with respect to FIG. 2, the cassette 28 may not be mounted on a cassette attaching portion 78. For this reason, it is possible to prevent the cassette 28 from being mounted in an erroneous orientation.

The flow path 42 formed in the cassette body 40 includes a first line 42a through which blood flows during operation of the centrifugal separator 14, a second line 42b through which blood does not flow during operation of the centrifugal separator 14, and a filter line 42c in which a filter member 70 is disposed. One end side 42a1 of the first line 42a and one end side 42c1 of the filter line 42c are connected via a first coupling portion 48. The other end side 42a2 of the first line 42a and the other end side 42c2 of the filter line 42c are connected via a second coupling portion 50.

One end side 42b1 of the second line 42b is connected to an intermediate portion of the first line 42a via a third coupling portion 51. The other end side 42b2 of the second line 42b is closed. The first line 42a and the filter line 42c at least partially extend in parallel. The second line 42b is formed in a straight line and is connected in series to a portion of the first line 42a extending in parallel with the filter line 42c. At least a part of the first line 42a extends between the second line 42b and the filter line 42c extending in parallel. Each of the first coupling portion 48, the second coupling portion 50, and the third coupling portion 51 is included in a part of the flow path 42.

In the cassette body 40, a seal portion 55 corresponding to welding positions is formed on both sides of the flow path 42 along the flow path 42. In addition, at the outer peripheral edge 40c of the cassette body 40, a seal portion 57 is formed along the outer peripheral edge 40c. In the cassette body 40 (excluding a convex portion forming the flow path 42), a portion other than the seal portions 55 and 57 corresponds to a non-sealed portion at which the first sheet 40a and the second sheet 40b are not welded to each other. The seal portion 55 is pressurized during formation, and thus has a smaller thickness than that of the non-sealed portion, and is recessed with respect to the non-sealed portion. In other words, the non-sealed portion protrudes in the thickness direction with respect to the seal portion 55.

A seal width of a seal portion 55a formed on both sides of the first pressure-receiving portion 60 in the seal portion 55 is set to be larger than a seal width of a seal portion 55b formed on both sides of a flow path adjacent to the first pressure-receiving portion 60. A seal width of a seal portion 55c formed on both sides of a second pressure-receiving portion 62 in the seal portion 55 is set to be larger than a seal width of a seal portion 55d formed on both sides of a flow path adjacent to the second pressure-receiving portion 62.

A wall portion of the cassette body 40 forming the flow path 42 convexly bulges in the thickness direction of the cassette 28 on both surface sides of the cassette body 40 even when no positive pressure acts in the flow path 42. Therefore, the flow path 42 is a flow path which is open in a natural state. The flow path 42 at a pressed position is elastically deformable in a closing direction at the time of being pressed by an external force.

The cassette body 40 includes a first line forming member 54 which forms a first line 42a and has a first load detection soft portion made of a soft material, and a second line forming member 56 which forms a second line 42b and has a second load detection soft portion made of a soft material. The first pressure-receiving portion 60 pressed by a first load detector 88 (described below), which is mounted on the centrifugal separator 14 in a cassette attached state in which the cassette 28 is attached to the centrifugal separator 14, is provided in the first line forming member 54. The first pressure-receiving portion 60 is included in the first load detection soft portion described above. The second pressure-receiving portion 62 pressed by a second load detector 90 (described below) mounted on the centrifugal separator 14 in the cassette attached state is provided in the second line forming member 56. The second pressure-receiving portion 62 is included in the second load detection soft portion described above.

Each of the first pressure-receiving portion 60 and the second pressure-receiving portion 62 is included in a part of the flow path 42. Therefore, the first pressure-receiving portion 60 and the second pressure-receiving portion 62 bulge from the sheet surface 41 (base surface) of the cassette body 40 in the thickness direction of the cassette body 40. The first pressure-receiving portion 60 and the second pressure-receiving portion 62 are formed to have the same shape and same size. Therefore, the first pressure-receiving portion 60 and the second pressure-receiving portion 62 have the same rigidity.

The cassette body 40 has a filter line forming member 64 forming the filter line 42c. A filter accommodating portion 64b accommodates the filter member 70 for removing a blood clump contained in blood or a blood component.

A plurality of clamping action portions 76 (76a to 76d), on which a plurality of clamps 72 (72a to 72d) (see FIG. 4) corresponding to a flow path opening/closing mechanism provided in the centrifugal separator 14 acts, is provided in the cassette 28. When the cassette 28 is mounted on the centrifugal separator 14, the clamping action portions 76 abuts on or face the corresponding clamps 72. Specifically, the clamping action portion 76a is provided at a position forming an end of the first line 42a on a side of the first port member 44 in the cassette 28. The clamping action portion 76b is provided between the second pressure-receiving portion 62 and the third coupling portion 51 (a position near the third coupling portion 51 of the second line 42b). Clamping action portions 76c and 76d are provided at positions forming both ends of the filter line 42c, respectively.

A flow path configuration formed in the cassette 28 and the number and arrangement of the bags to be provided are not limited to the configuration described above and illustrated and may be altered according to a type of blood component to be collected, a usage method, etc.

An inflow line for sending blood (whole blood) or a blood component collected from the donor or to the centrifugal separator 14, a return line for returning a predetermined blood component to the donor, and a cavity 59 through which blood and blood components do not flow are provided in the cassette body 40. In addition, a plurality of fluid passages 61a to 61e for sending whole blood or a predetermined blood component collected from the donor, a plurality of branch portions 63a to 63c for branching the plurality of fluid passages 61a to 61e, a first port 43a connected to a blood collecting portion for collecting blood from the donor, and a second port 43b connected to the blood processing unit 16 for separating whole blood or a predetermined blood component are provided inside the cassette body 40.

In the case of the present embodiment, the first line 42a is included in a part of the inflow line, the filter line 42c is included in a part of the return line, and the second line 42b is included in the cavity 59. The second line forming member 56 is a cavity forming member that forms the cavity 59. The inflow line has the fluid passages 61a to 61d. The return line has fluid passages 61a, 61d, and 61e. The inflow line and the return line share the fluid passages 61a and 61d. The branch portion 63a is included in the first coupling portion 48. The branch portion 63b is included in the second coupling portion 50. The branch portion 63c is included in the third coupling portion 51. The cavity 59 communicates with the first line 42a (the fluid passages 61b and 61c) via the third coupling portion 51.

The first coupling portion 48 is included in a branch portion that branches one fluid passage 61a into two fluid passages 61b and 61e and is included in a merging portion that merges the two fluid passages 61b and 61e into the one fluid passage 61a. The second coupling portion 50 is included in a merging portion that merges two fluid passages 61c and 61e to one fluid passage 61d and is included in a branch portion that branches the one fluid passage 61d into the two fluid passages 61b and 61e.

The inflow line and the return line include a first fluid passage 67a in which the first pressure-receiving portion 60 is provided and a second fluid passage 67b provided in parallel with the first fluid passage 67a. In the present embodiment, the first line 42a is included in the first fluid passage 67a, and the filter line 42c is included in the second fluid passage 67b. In the cassette body 40, a notch 69 is provided between the first fluid passage 67a and the second fluid passage 67b. The notch 69 penetrates the cassette body 40 in the thickness direction.

The inflow line and the return line may correspond to a common line. The inflow line and the return line may correspond to lines independent of each other.

The first coupling portion 48 (branch portion or merging portion) is configured so that a flow direction of a fluid changes in the first coupling portion 48. Specifically, the one end side 42a1 of the first line 42a is connected to the filter line 42c so as to be inclined toward the second end 45b side of the cassette body 40. A connection angle θ1 between the fluid passage 61a and the fluid passage 61b is, for example, 90 to 150 degrees, preferably 110 to 135 degrees.

The second coupling portion 50 (branch portion or merging portion) is configured so that a flow direction of a fluid changes in the second coupling portion 50. Specifically, the other end side 42a2 of the first line 42a is connected to the filter line 42c so as to be inclined toward the first end 45a side of the cassette body 40. A connection angle θ2 between the fluid passage 61c and the fluid passage 61d is, for example, 90 to 150 degrees, preferably 110 to 135 degrees.

The third coupling portion 51 is configured so that a flow direction of a fluid changes in the third coupling portion 51. Specifically, the fluid passage 61c is connected to the fluid passage 61b so as to be inclined toward the second end 45b side of the cassette body 40. A connection angle θ3 between the fluid passage 61b and the fluid passage 61c is, for example, 90 to 150 degrees, preferably 110 to 135 degrees.

A flow path diameter of the first coupling portion 48 is smaller than a flow path diameter of a line adjacent to the first coupling portion 48. A flow path diameter of the second coupling portion 50 is smaller than a flow path diameter of a line adjacent to the second coupling portion 50. A flow path diameter of the third coupling portion 51 is smaller than a flow path diameter of a line adjacent to the third coupling portion 51. That is, the first coupling portion 48, the second coupling portion 50, and the third coupling portion 51 are configured to be thinner than the other lines in the flow path 42.

Figure 3A:
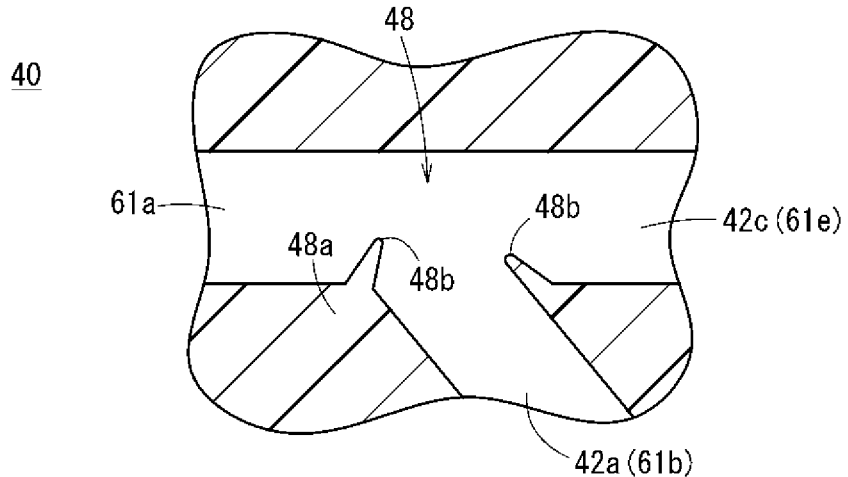
FIG. 3A is an explanatory diagram of a configuration of a first coupling portion having a protrusion.
Figure 3B:
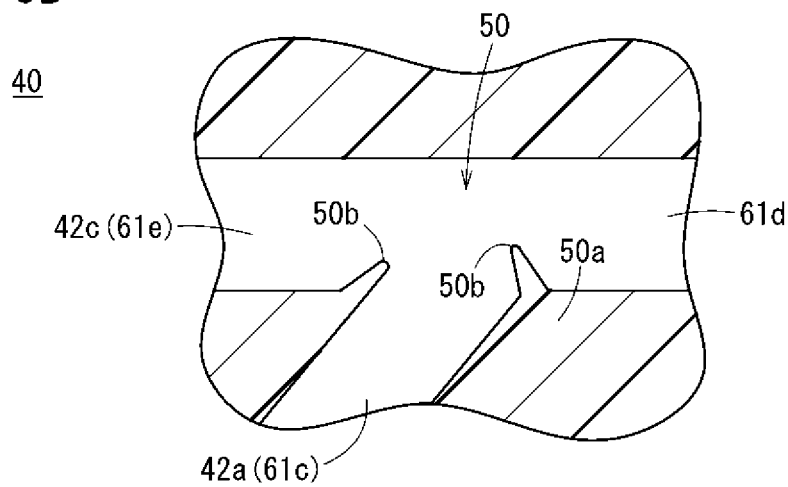
FIG. 3B is an explanatory diagram of a configuration of a second coupling portion having a protrusion.
Figure 3C:
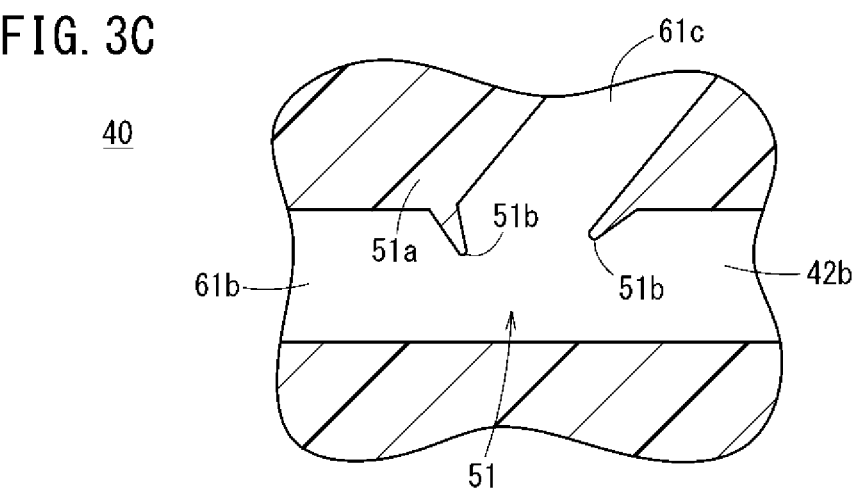
FIG. 3C is an explanatory diagram of a configuration of a third coupling portion having a protrusion.

As illustrated in FIG. 3A, the first coupling portion 48 may have a protrusion 48b partially protruding from an inner wall 48a into the flow path. As illustrated in FIG. 3B, the second coupling portion 50 may have a protrusion 50b partially protruding from an inner wall 50a into the flow path. As illustrated in FIG. 3C, the third coupling portion 51 may have a protrusion 51b partially protruding from an inner wall 51a into the flow path.

A method of manufacturing the cassette 28 having the above-described configuration includes a molding process of superposing the first sheet 40a and the second sheet 40b, welding the first sheet 40a and the second sheet 40b to form the flow path 42 between the first sheet 40a and the second sheet 40b, thereby molding the cassette 28 having the cassette body 40, and a sterilization step of sterilizing the cassette 28 obtained by the molding process.

In the molding process, for example, sheet-like materials are drawn from two material rolls obtained by winding the sheet-like materials corresponding to materials of the first sheet 40a and the second sheet 40b around the two material rolls, respectively, and supplied to a joining device such as a high frequency welding device together with assembled parts (the filter member 70 and the port members 44 and 46). The joining device has upper and lower molds, and blow molding is performed while joining the two sheet-like materials together with the assembled parts to mode the cassette 28 in which the flow path 42 is formed. In this case, the tubes 32 and 34 may be connected at the time of molding the cassette 28 using the joining device.

In a sterilization process, the whole blood collection circuit set 12 including the plurality of bags 24 (ACD solution bag 24a, etc.) may be sterilized. In this way, the blood collection circuit set 12 can be efficiently sterilized.

In FIG. 1, the centrifugal separator 14 is a device repeatedly used in blood component collection, and is provided, for example, in a medical facility, a blood collecting vehicle, etc. The centrifugal separator 14 includes the centrifugal unit 18 having the rotor 18a and the cassette attaching portion 78 configured to allow the cassette 28 of the blood collection circuit set 12 to be attached thereto.

Figure 4:
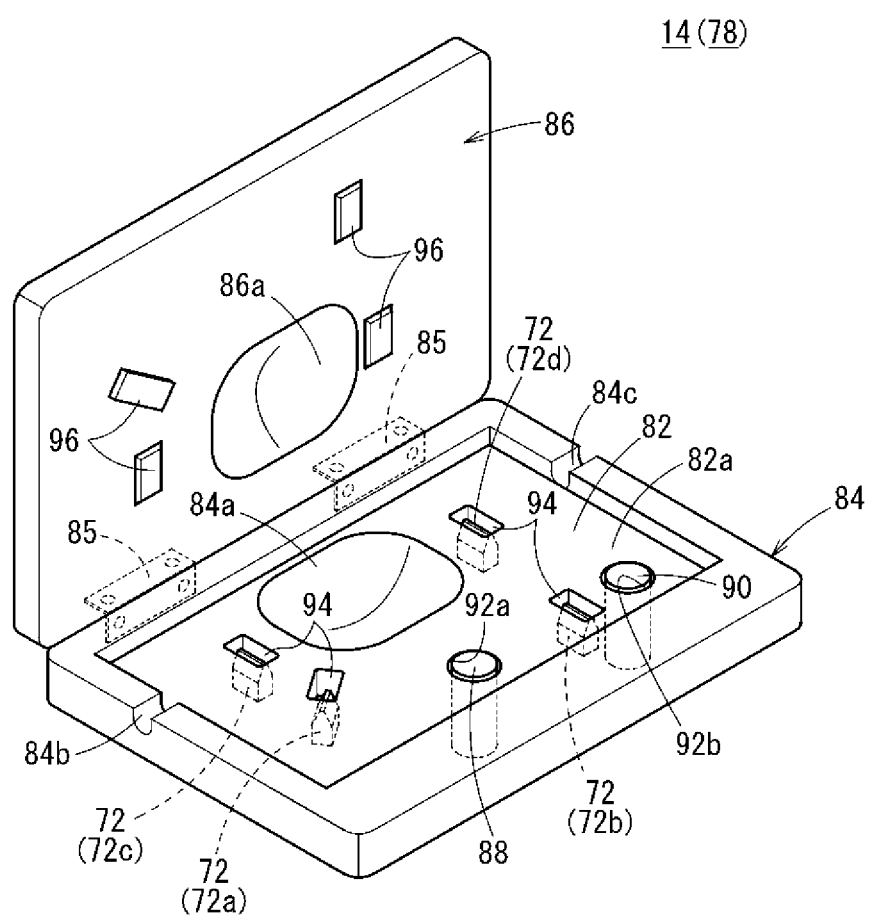
FIG. 4 is a perspective view of a cassette attaching portion.

As illustrated in FIG. 4, the cassette attaching portion 78 includes an attachment base 84 having a cassette mounting groove 82 formed therein, an openable and closable lid body 86 configured to cover the attachment base 84 when closed, a first load detector 88 capable of pressing the first pressure-receiving portion 60 of the cassette 28 (see FIG. 2), a second load detector 90 capable of pressing the second pressure-receiving portion 62 (see FIG. 2) of the cassette 28, and the plurality of clamps 72 configured to be capable of pressing the clamping action portion 76 of the cassette 28.

A first port arrangement groove 84b in which the first port member 44 of the cassette 28 can be disposed and a second port arrangement groove 84c in which the second port member 46 of the cassette 28 can be disposed are provided on the outer periphery of the attachment base 84. The first port arrangement groove 84b and the second port arrangement groove 84c are in communication with the cassette mounting groove 82.

The lid body 86 is rotatably connected to the attachment base 84 via a hinge 85. When the lid body 86 is closed in a state in which the cassette 28 is held in the cassette mounting groove 82 of the attachment base 84, the cassette 28 is interposed between the attachment base 84 and the lid body 86. The attachment base 84 and the lid body 86 are provided with recesses 84a and 86a, each of which can receive the filter accommodating portion 64b of the cassette 28. In this way, the filter accommodating portion 64b is prevented from being crushed while properly holding the cassette 28 between the attachment base 84 and the lid body 86. In addition, the recesses 84a and 86a prevent the filter accommodating portion 64b from excessively swelling.

The first load detector 88 is inserted into a first through-hole 92a provided in the attachment base 84 and exposed in the cassette mounting groove 82. An upper surface of the first load detector 88 protrudes from a bottom surface 82a of the cassette mounting groove 82. The second load detector 90 is inserted into a second through-hole 92b provided in the attachment base 84 and exposed in the cassette mounting groove 82. An upper surface of the second load detector 90 protrudes from the bottom surface 82a of the cassette mounting groove 82. A protrusion height of the first load detector 88 from the bottom surface 82a is the same as a protrusion height of the second load detector 90 from the bottom surface 82a. For example, the first load detector 88 and the second load detector 90 include load cells.

The plurality of clamps 72 (72a to 72d) can advance and retreat in the thickness direction of the cassette 28 in a state held in the cassette mounting groove 82, and are disposed to correspond to arrangement of the plurality of clamping action portions 76 (76a to 76d) provided in the cassette 28. The plurality of clamps 72 can press the plurality of clamping action portions 76, respectively, via a plurality of holes 94 opening to the bottom surface 82a of the cassette mounting groove 82. In the lid body 86, a plurality of projections 96 is provided at positions corresponding to the plurality of holes 94 (clamps 72) when closed.

When the clamping action portion 76 is not pressed by the clamp 72 in a state in which the cassette 28 is attached to the cassette attaching portion 78, the flow path in the clamping action portion 76 is open. When the clamp 72 protrudes from the hole 94 and presses the clamping action portion 76, the flow path in the clamping action portion 76 is blocked. Further, when the clamp 72 moves backward, due to an elastic restoring force of the cassette body 40 (clamping action portion 76), the clamping action portion 76 returns to an original shape and the flow path in the clamping action portion 76 opens.

As illustrated in FIG. 1, the centrifugal separator 14 includes an ACD solution transfer pump 98 acting on the ACD solution transfer tube 23 and a blood collection/blood return pump 100 acting on the processing unit-side tube 34 connected to the cassette 28. The ACD solution transfer pump 98 is a pump that transfers the ACD solution from the ACD solution bag 24a to the cassette 28 and the blood processing unit 16 via the ACD solution transfer tube 23. The blood collection/blood return pump 100 is a pump that transfers blood from the donor side to the blood processing unit 16 and transfers blood from the blood processing unit 16 to the donor. For example, the ACD solution transfer pump 98 and the blood collection/blood return pump 100 include a roller pump and a finger pump.

The centrifugal separator 14 further includes a controller 102 that controls the centrifugal unit 18, the cassette attaching portion 78, and the pumps 98 and 100. Operations of the plurality of clamps 72 are controlled by the controller 102. The controller 102 has an arithmetic unit 103 that obtains (calculates) a circuit internal pressure of the blood collection circuit set 12 based on a load detected by the first load detector 88 and the second load detector 90 (FIG. 4) when the centrifugal separator 14 is in operation.

Next, a description will be given of an operation of the blood component collection system 10 according to the present embodiment configured as described above.

As a preparation (set-up) for collecting a blood component from the donor using the blood component collection system 10 illustrated in FIG. 1, the blood collection circuit set 12 is attached to the centrifugal separator 14.

Specifically, the cassette 28 is attached to the cassette attaching portion 78, and the blood processing unit 16 is attached to the rotor 18a. On the other hand, the blood collection needle 20 pierces the donor.

Figure 5:
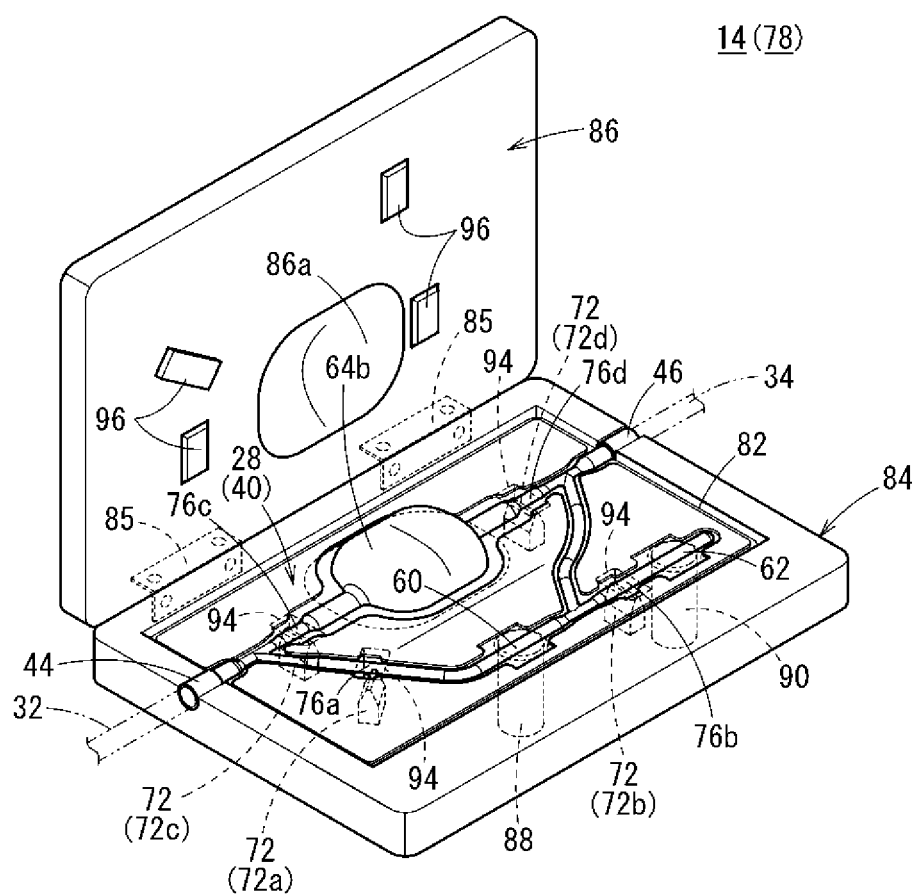
FIG. 5 is a perspective view of the cassette attaching portion in a state in which the blood component collection cassette is placed.

When the cassette 28 is attached to the cassette attaching portion 78, as illustrated in FIG. 5, the cassette 28 is first mounted in the cassette mounting groove 82. Further, when the lid body 86 is closed, the cassette 28 is held between the attachment base 84 and the lid body 86. As a result, the first pressure-receiving portion 60 and the second pressure-receiving portion 62 of the cassette 28 are pressed by the first load detector 88 and the second load detector 90, and are in a state of being slightly elastically deformed. In this case, the amount of deformation of the first pressure-receiving portion 60 due to being pressed by the first load detector 88 is the same as the amount of deformation of the second pressure-receiving portion 62 due to being pressed by the second load detector 90. In addition, the plurality of clamping action portions 76 of the cassette 28 is placed opposite to the plurality of clamps 72.

When the centrifugal separator 14 illustrated in FIG. 1 is instructed to start an operation by an operation of the user, priming using the ACD solution is executed under action of the ACD solution transfer pump 98 in the centrifugal separator 14. Specifically, in the priming, the ACD solution is introduced from the ACD solution bag 24a to the flow path 42 in the cassette 28 via the ACD solution transfer tube 23, and the priming using the ACD solution is terminated in a stage in which it is detected by a line sensor (not illustrated) disposed outside the cassette 28 that the ACD solution has reached the vicinity of the first port 43a.

Subsequently, the centrifugal separator 14 applies a centrifugal force to the blood processing unit 16 attached to the rotor 18a by rotating the rotor 18a, and operates the blood collection/blood return pump 100 to extract blood (whole blood) from the donor and introduce blood into the blood processing unit 16 (blood collection operation). The blood introduced into the blood processing unit 16 is separated into red blood cells (concentrated red blood cells), buffy coat and plasma (platelet poor plasma) by a centrifugal force accompanying rotation of the rotor 18a.

The plasma separated in the blood processing unit 16 is introduced into the PPP bag 24b via a PPP transfer tube 36. The remaining blood components (erythrocytes and buffy coat) are returned to the donor after centrifugation (blood return operation). In this instance, foreign matter such as blood clumps, etc. contained in the remaining blood components is trapped by the filter member 70 provided on the filter line 42c of the cassette 28, and thus it is possible to reduce a risk of foreign matter returning to the donor. The blood collection operation and the blood return operation described above are repeated a plurality of times.

When the blood component collection system 10 is in operation, the clamp 72 (FIG. 4) of the centrifugal separator 14 operates as follows.

Figure 6:
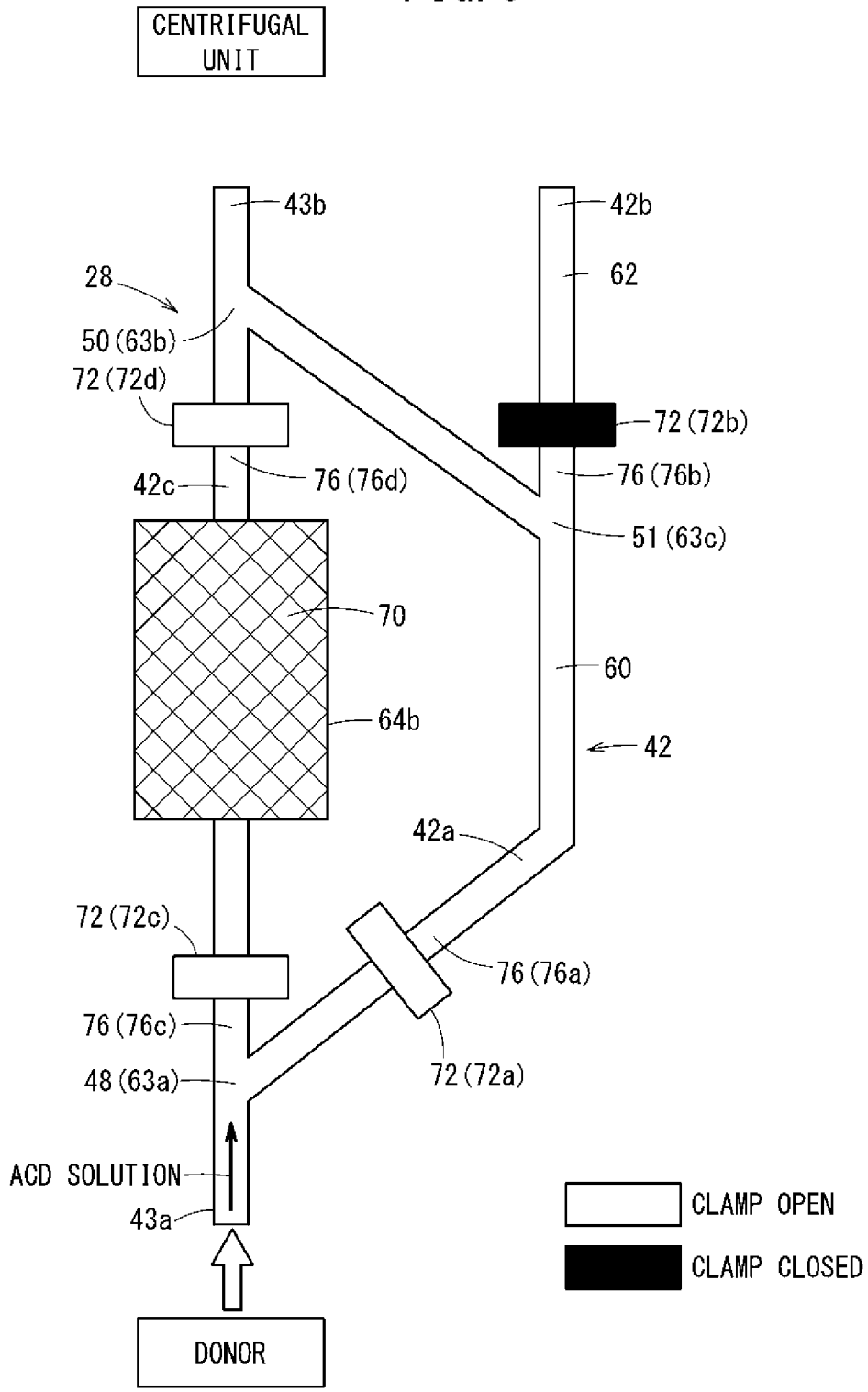
FIG. 6 is a first explanatory diagram for description of an operation of a clamp.

As illustrated in FIG. 6, when priming is performed using the ACD solution, the clamp 72b is closed, and the clamps 72a, 72c, and 72d are opened. In this way, the second line 42b is cut off from the other flow path 42. In addition, in this state, the priming using the ACD solution is terminated in a stage in which it is detected by a line sensor (not illustrated) outside the cassette 28 nearest to the first port 43a that the ACD solution has reached the vicinity of the first port 43a.

Figure 7:
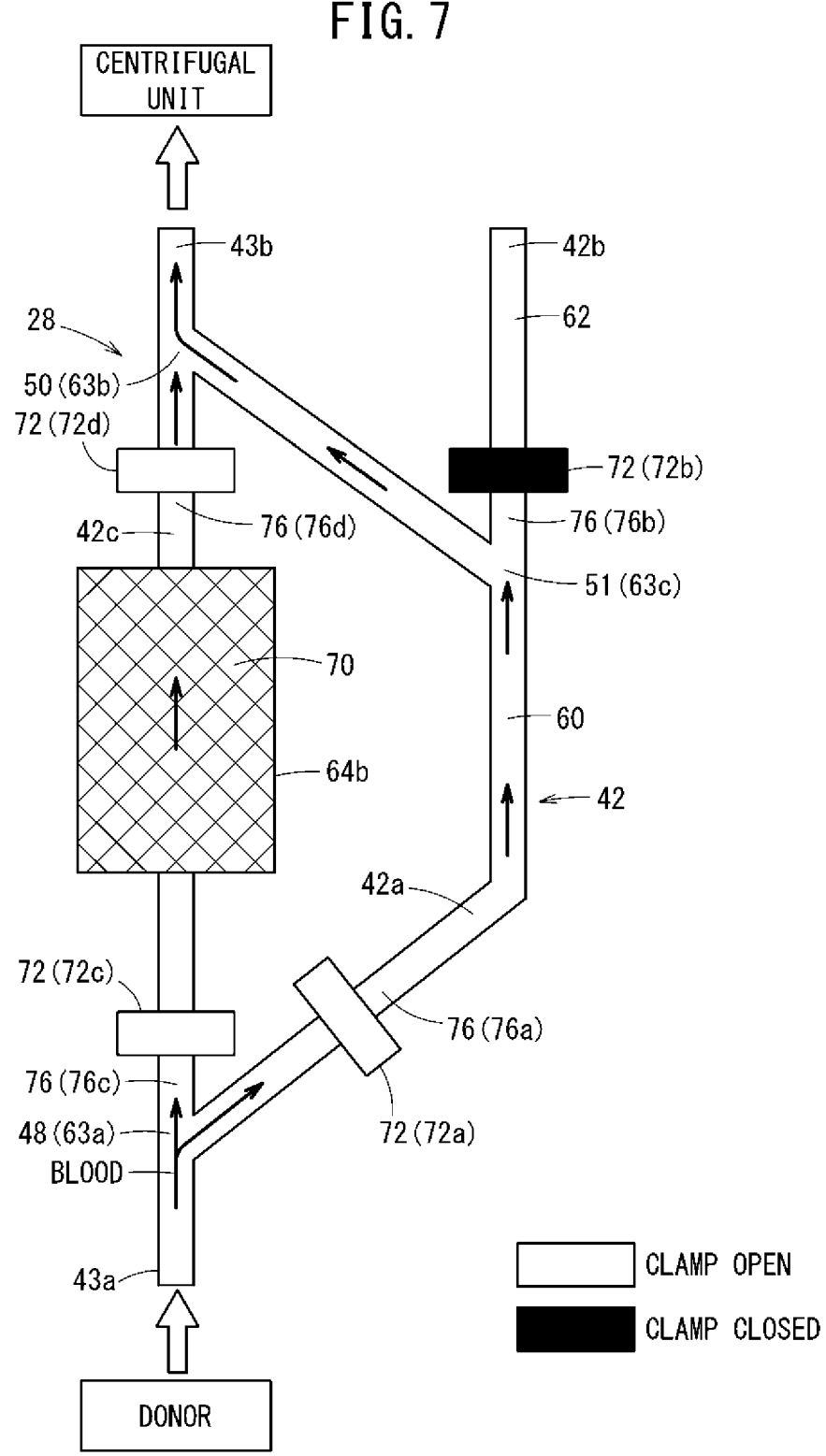
FIG. 7 is a second explanatory diagram for description of an operation of the clamp.

Subsequently, at the time of performing first blood collection, as illustrated in FIG. 7, a state in which the clamp 72b is closed and the clamps 72a, 72c, and 72d are open is maintained. Then, in this state, blood from the donor is introduced into the flow path 42 other than the second line 42b of the cassette 28, and all air in a circuit of the cassette 28 is pushed out to the blood processing unit 16 by the blood.

Figure 8:
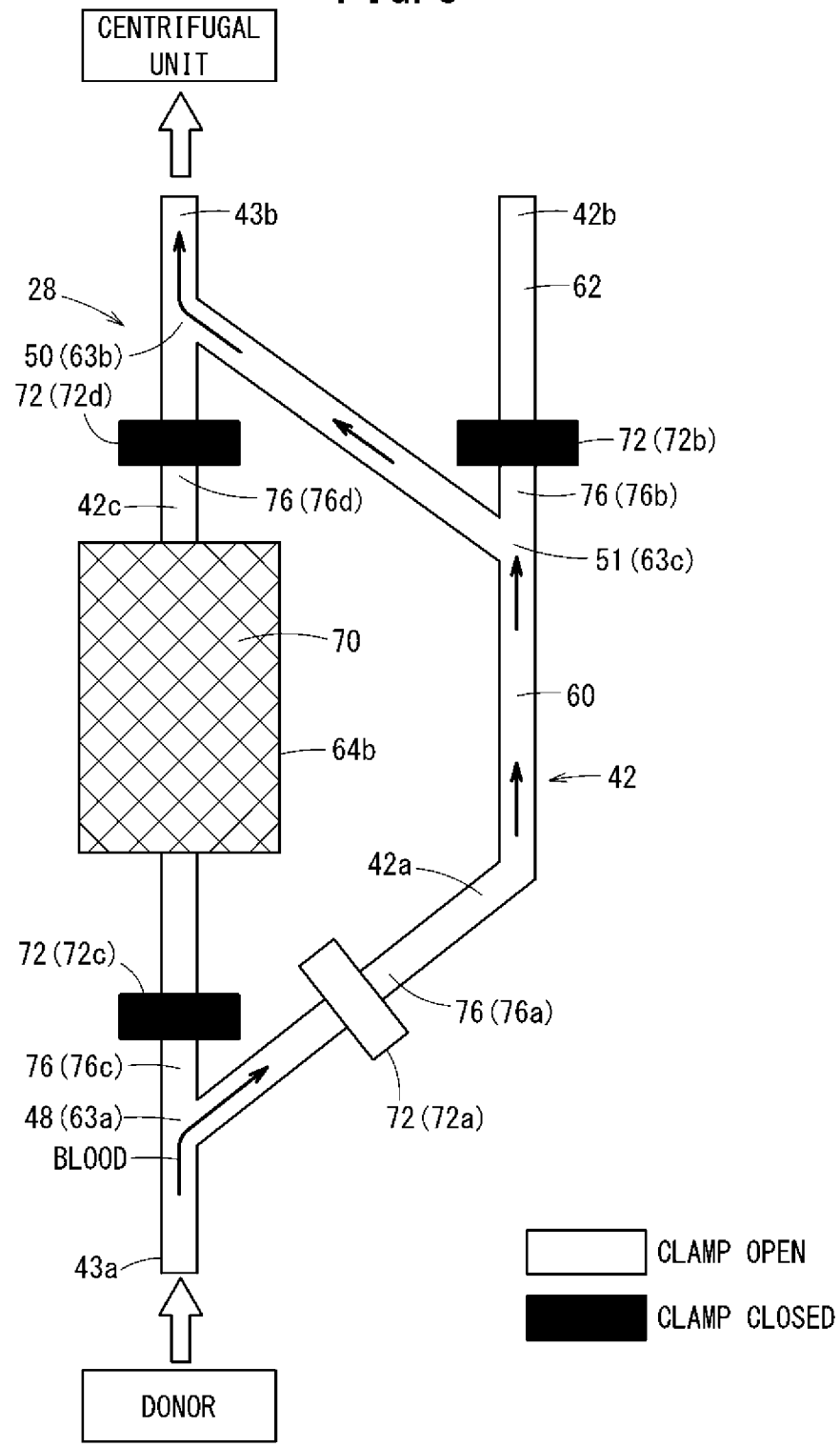
FIG. 8 is a third explanatory diagram for description of an operation of the clamp.

During the first blood collection, as illustrated in FIG. 8, the filter line 42c is closed by closing the clamps 72c and 72d, which prevents negative pressure from acting on the filter accommodating portion 64b and blocking the filter accommodating portion 64b.

In this way, whole blood is introduced from a first inlet (first port 43a) provided in the cassette 28 to the inflow line (fluid passages 61a to 61d) of the cassette 28. Branching into the inflow line and a first branch line (filter line 42c) occurs at a first branch portion (first coupling portion 48) provided at a downstream of the first inlet. The inflow line and the first branch line merge via a first merging portion (second coupling portion 50). When the whole blood flows through the inflow line, the whole blood flows from a first outlet (second port 43b) provided in the cassette 28 to the centrifugal separator 14 via the first branch portion and the first merging portion.

Figure 9:
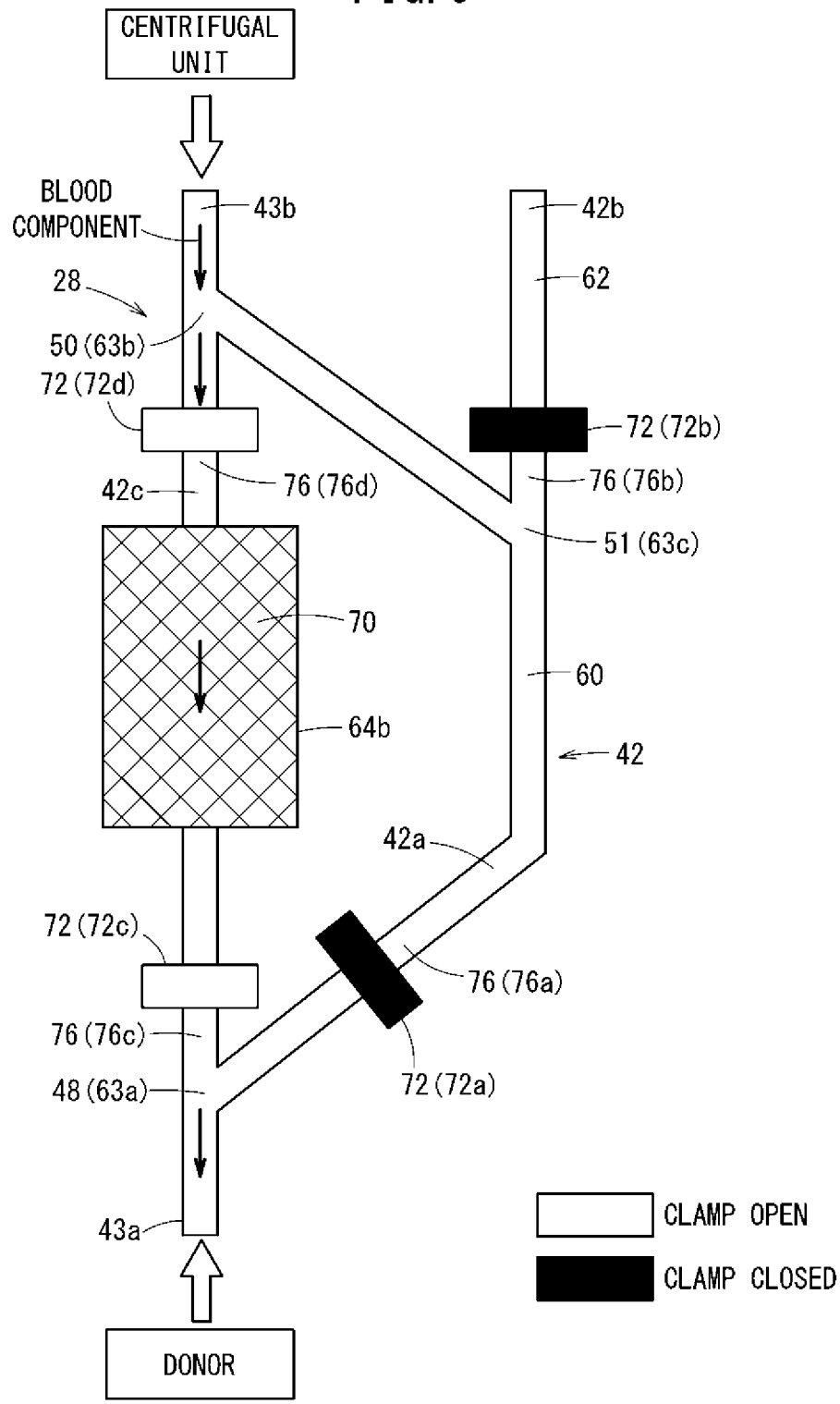
FIG. 9 is a fourth explanatory diagram for description of an operation of the clamp.

Subsequently, when a blood component is returned to the donor, as illustrated in FIG. 9, the clamp 72a is closed and the clamps 72c and 72d are opened, thereby closing the first line 42a and opening the filter line 42c. Therefore, when a blood component passes through the filter member 70, a blood clump contained in the blood component is trapped in the filter member 70. Since the first line 42a is closed, no foreign matter is returned to the donor via the first line 42a.

Subsequently, when blood collection is performed for the second time and thereafter, as illustrated in FIG. 10, the clamps 72c and 72d are closed and the clamp 72a is opened, thereby closing the filter line 42c and opening the first line 42a. Accordingly, blood is transferred to the blood processing unit 16 side (the centrifugal unit 18 side) via only the first line 42a in the first line 42a and the filter line 42c. Thereafter, blood return (FIG. 9) is performed again. Such blood collection and blood return are repeated a plurality of times.

Further, when final blood return is performed, as illustrated in FIG. 9, the clamp 72a is closed and the clamps 72c and 72d are opened.

As described above, at least one blood component among predetermined blood components separated by the centrifugal separator 14 is introduced to the return line (fluid passages 61d, 61e, and 61a) via a second inlet (second port 43b) provided in the cassette 28. Then, at the second branch portion (second coupling portion 50) provided at a downstream of the second inlet, the return line and the second branch line (first line 42a) are branched. The return line and the second branch line merge via the second merging portion (the first coupling portion 48). In the present embodiment in which at least one blood component flows out from the second outlet (first port 43a) provided in the cassette 28 toward the donor via the second branch portion and the second merging portion at the time of flowing through the return line, the first port 43a serves both as the first inlet and the second outlet. The second port 43b serves as both the first outlet and the second inlet.

A flow path internal pressure detection method includes a first measurement step, a second measurement step, a load calculation step, and an internal pressure calculation step. In the first measurement step, the first line forming member 54 in a state in which blood is being sent to the first line 42a is pressed, and a load α1 caused by pressing of the first line forming member 54 is measured.

Specifically, a load received from the first pressure-receiving portion 60 is detected by the first load detector 88. In the second measurement step, the second line forming member 56 in a state in which no blood is being sent to the second line 42b is pressed, and a load α2 caused by pressing of the second line forming member 56 is measured. Specifically, a load received from the second pressure-receiving portion 62 is detected by the second load detector 90.

In the load calculation step, a differential load α obtained by subtracting the load α2 measured in the second measurement step from the load α1 measured in the first measurement step is calculated. In the internal pressure calculation step, an internal pressure of the first line 42a is calculated based on the calculated differential load α. In practice, a reaction force based on an elastic restoring force of the first pressure-receiving portion 60 may not be completely equal to a reaction force based on an elastic restoring force of the second pressure-receiving portion 62. For this reason, before calculating the differential load α, a step of adjusting α1 and α2 to be equal to each other is performed under the same condition (in a state in which no blood is sent to either the first line 42a or the second line 42b). More specifically, a correction coefficient A for equalization is calculated, and a correction step for establishing α1=correction coefficient A×α2 is performed. Thereafter, the differential load α is calculated.

In this case, the cassette 28 according to the present embodiment has the following effects.

The cassette 28 includes an inflow line for sending blood or a blood component collected from the donor to the centrifugal separator 14, a return line for returning a predetermined blood component to the donor, and the first pressure-receiving portion 60 provided in the line forming member forming one of the inflow line and the return line and pressed by the first load detector 88 in the attached state in which the cassette 28 is attached to the centrifugal separator 14, and at least the first pressure-receiving portion 60 is made of a soft material. For this reason, the cassette 28 can be manufactured at a lower cost when compared to a conventional cassette made of a hard resin manufactured by injection molding. In addition, since the first pressure-receiving portion 60 pressed by the first load detector 88 is provided, the circuit internal pressure can be measured based on a load detected by the first load detector 88 of the centrifugal separator 14.

Examples of the sterilization process at the time of manufacturing the cassette 28 illustrated in FIG. 2, etc. include EOG sterilization, autoclave sterilization, etc.

According to the blood component collection system 10, it is possible to accurately measure the circuit internal pressure (negative pressure and positive pressure) based on the load detected by the first load detector 88 (FIG. 4) of the centrifugal separator 14 and the load detected by the second load detector 90 (FIG. 4) of the centrifugal separator 14. The circuit internal pressure is calculated by the arithmetic unit 103 (FIG. 1) of the centrifugal separator 14. For example, the internal circuit pressure to be measured is in a range of −300 to 500 mmHg.

Figure 11A:
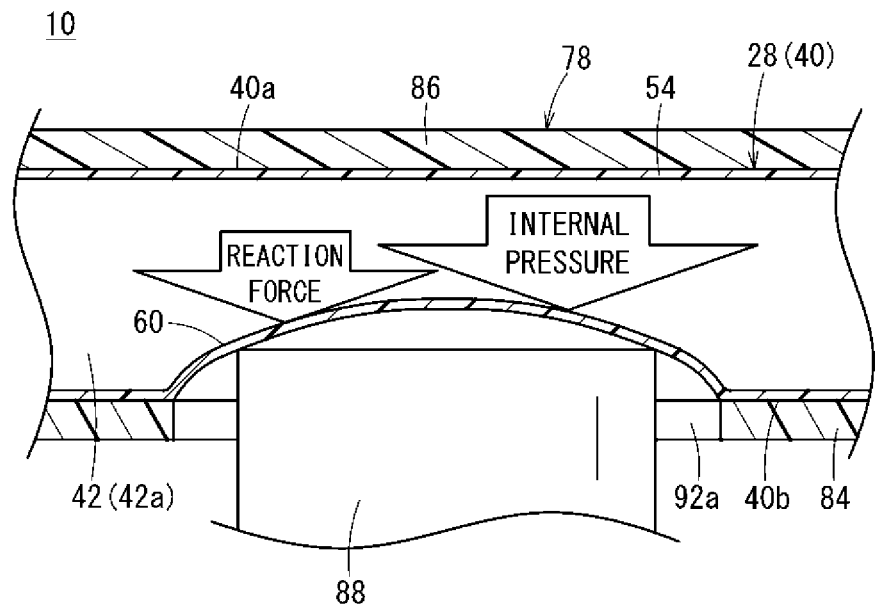
FIG. 11A is a diagram for description of load detection at the time of a positive pressure.
Figure 11B:
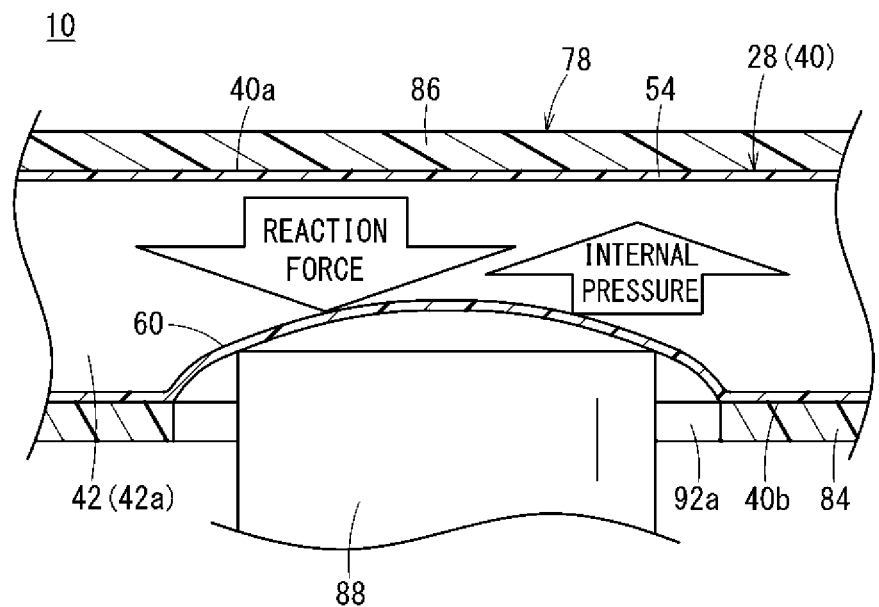
FIG. 11B is a diagram for description of load detection at the time of a negative pressure.

Specifically, a load obtained by adding an internal pressure (circuit internal pressure) of the first line 42a through which blood flows and a reaction force of the first pressure-receiving portion 60 (restoring force due to deformation of the first pressure-receiving portion 60) is detected by the first load detector 88. That is, when the circuit internal pressure is positive, as illustrated in FIG. 11A, load (pressing force from the first pressure-receiving portion 60) acting on the first load detector 88 is calculated by simply adding the circuit internal pressure and reaction force. On the other hand, when the circuit internal pressure is negative, as illustrated in FIG. 11B, the load acting on the first load detector 88 is obtained by subtracting an absolute value of the circuit internal pressure from the reaction force.

In the blood component collection system 10, a load due to a reaction force of the second pressure-receiving portion 62 is detected by the second load detector 90. To block the second line 42b in a state of a normal pressure, an internal pressure of the second line 42b corresponds to 0 mmHg at all times. For this reason, the load detected by the second load detector 90 only corresponds to the reaction force of the second pressure-receiving portion 62 (restoring force due to deformation of the second pressure-receiving portion 62). Then, a reaction force of the second pressure-receiving portion 62 acting on the second load detector 90 is the same as a reaction force of the first pressure-receiving portion 60 acting on the first load detector 88 when the above-described correction step is performed. Therefore, when the load detected by the second load detector 90 is subtracted from the load detected by the first load detector 88, a load due to the internal pressure of the first line 42a through which blood flows is obtained. Therefore, it is possible to calculate the circuit internal pressure based on the load due to the internal pressure of the first line 42a. In this case, the controller 102 of the centrifugal separator 14 stores a calibration curve (calibration curve data) showing a relationship between a load and a circuit internal pressure, and can calculate a circuit internal pressure using an obtained load and the calibration curve data.

Figure 12:
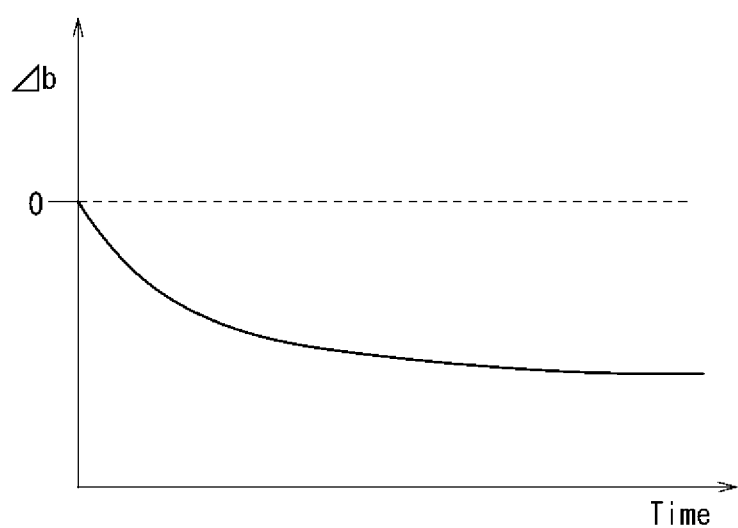
FIG. 12 is a diagram for description of a decrease in reaction force over time.

As illustrated in FIG. 12, the reaction force of the first pressure-receiving portion 60 decreases over time. FIG. 12 illustrates an image of a time change (Ab) of the reaction force of the first pressure-receiving portion 60 when an initial reaction force is set to 0. The reaction force of the first pressure-receiving portion 60 decreases over time as described above since creep occurs as a state in which the first pressure-receiving portion 60 is pressed by the first load detector 88 continues. Therefore, when a fixed value that does not change over time is used as the reaction force of the first pressure-receiving portion 60, measurement accuracy of the circuit internal pressure decreases.

Therefore, in the blood component collection system 10, similarly to the reaction force of the first pressure-receiving portion 60, a load due to the reaction force of the second pressure-receiving portion 62 decreasing over time is detected in real time and used for calculation of the circuit internal pressure. In this way, it is possible to eliminate a measurement error due to the decrease in reaction force over time, and to suppress a decrease in measurement accuracy of the circuit internal pressure. In other words, since the reaction force of the first pressure-receiving portion 60 corresponds to an intercept of a function representing the above-described calibration curve, in the present invention, it is possible to eliminate the measurement error due to the decrease of the reaction force over time by correcting the intercept of the calibration curve in real time using the load detected by the second load detector 90 (reaction force of the second pressure-receiving portion 62).

When compared to a high pressure region, in a low pressure region, a reaction force is relatively large, and thus an influence on the measurement error tends to be large. On the other hand, according to the present invention, it is possible to accurately measure the circuit internal pressure by detecting the reaction force that changes over time in real time to use the detected reaction force, thereby eliminating the measurement error.

In addition, in the cassette 28, the first line 42a and the second line 42b communicate with each other in a natural state in which the cassette body 40 is not elastically deformed (the cavity 59 communicates with either one of the inflow line and the return line via the third coupling portion 51). Further, the centrifugal separator 14 includes the clamp 72b capable of pressing the cassette body 40 to close the flow path 42 between the first line 42a and the second line 42b. According to this configuration, in a manufacturing process of the cassette body 40, the first line 42a and the second line 42b can be simultaneously formed by blow molding. That is, the cavity 59 can be easily formed. In addition, when the centrifugal separator 14 is in operation, it is possible to reliably and easily prevent blood from flowing to the second line 42b by pressing a predetermined position of the cassette body 40 using the clamp 72b.

The clamping action portion 76b, on which the clamp 72b corresponding to the flow path opening/closing mechanism included in the centrifugal separator 14 acts, is provided between the third coupling portion 51 and the second pressure-receiving portion 62. According to this configuration, when the centrifugal separator 14 is in operation, it is possible to easily construct the cavity 59 not communicating with the inflow line and the return line.

Each of the first coupling portion 48, the second coupling portion 50, and the third coupling portion 51 (the branch portion or the merging portion) is configured such that a change in flow direction of a fluid in the coupling portion corresponds to an obtuse angle. According to this configuration, it is possible to reduce damage to blood when blood flows through each coupling portion.

Each of the flow path diameters of the first coupling portion 48, the second coupling portion 50, and the third coupling portion 51 (the branch portion or the merging portion) is smaller than the flow path diameter of the line adjacent to the coupling portion. According to this configuration, it is possible to inhibit the flow paths of the first coupling portion 48, the second coupling portion 50, and the third coupling portion 51 from being crushed.

As in FIG. 3A to FIG. 3C, a configuration in which the first coupling portion 48, the second coupling portion 50, and the third coupling portion 51 have the protrusions 48b, 50b, and 51b partially protruding from the inner walls 48a, 50a, and 51a into the flow paths, respectively, may inhibit the flow path of the coupling portion from being crushed.

The first port member 44 and the second port member 46 made of a hard material are provided at the outer peripheral edge 40c of the cassette 28. According to this configuration, the cassette 28 can be accurately attached to a predetermined position of the centrifugal separator 14.

In the cassette body 40, the notch 69 is provided between the first line 42a and the filter line 42c (between the first fluid passage 67a and the second fluid passage 67b). According to this configuration, when deformation occurs in the filter line 42c (the second fluid passage 67b), it is possible to prevent an influence of the deformation on the first line 42a (the first fluid passage 67a) in which the first pressure-receiving portion 60 is provided.

In the seal portion 55, the seal width of the seal portion 55a formed on both sides of the first pressure-receiving portion 60 is set to be larger than the seal width of the seal portion 55b formed on both sides of the flow path adjacent to the first pressure-receiving portion 60. In addition, in the seal portion 55, the seal width of the seal portion 55c formed on both sides of the second pressure-receiving portion 62 is set to be larger than the seal width of the seal portion 55d formed on both sides of the flow path adjacent to the second pressure-receiving portion 62. According to this configuration, it is possible to prevent the non-sealed portion (a portion adjacent to the seal portion 55 and having a larger thickness than that of the seal portion 55) in the cassette body 40 from coming into contact with the first load detector 88 and the second load detector 90.

When respective parts of the seal portion 55a and the seal portion 55b are cut out (an opening penetrating the cassette body 40 in the thickness direction is provided) on both sides of the first pressure-receiving portion 60 and the second pressure-receiving portion 62, it is possible to prevent the non-sealed portion in the cassette body 40 from coming into contact with the first load detector 88 and the second load detector 90.

A portion (filter member 70) for capturing a blood clump is provided in the cassette body 40. In this way, the number of operations of an operator (process of attaching the filter member 70) is reduced, and usability is improved.

In the above-described cassette 28, the flow path 42 is formed between the first sheet 40a and the second sheet 40b made of a soft material. However, a structure for forming the flow path 42 is not limited to such a configuration. For example, a member of the cassette body 40 forming the flow path 42 may correspond to a tube. In this case, the cassette body 40 includes a first tube (first line forming member) having a flow path included in the first line 42a, a second tube (second line forming member) having a flow path included in the second line 42b, and a third tube included in the filter line 42c, and includes a plate-like cassette base for supporting the first tube, the second tube, and the third tube.

The first pressure-receiving portion 60 and the clamping action portion 76a are provided in the first tube. The second pressure-receiving portion 62 and the clamping action portion 76b are provided in the second tube. The clamping action portions 76c and 76d are provided in the third tube. The cassette base is formed such that the first pressure-receiving portion 60 and the second pressure-receiving portion 62 are exposed, so that the first load detector 88 can press the first pressure-receiving portion 60 and the second load detector 90 can press the second pressure-receiving portion 62. In addition, the cassette base is formed such that the clamping action portions 76a to 76d are exposed, so that the clamps 72a to 72d can press the clamping action portions 76a to 76d.

Figure 13:
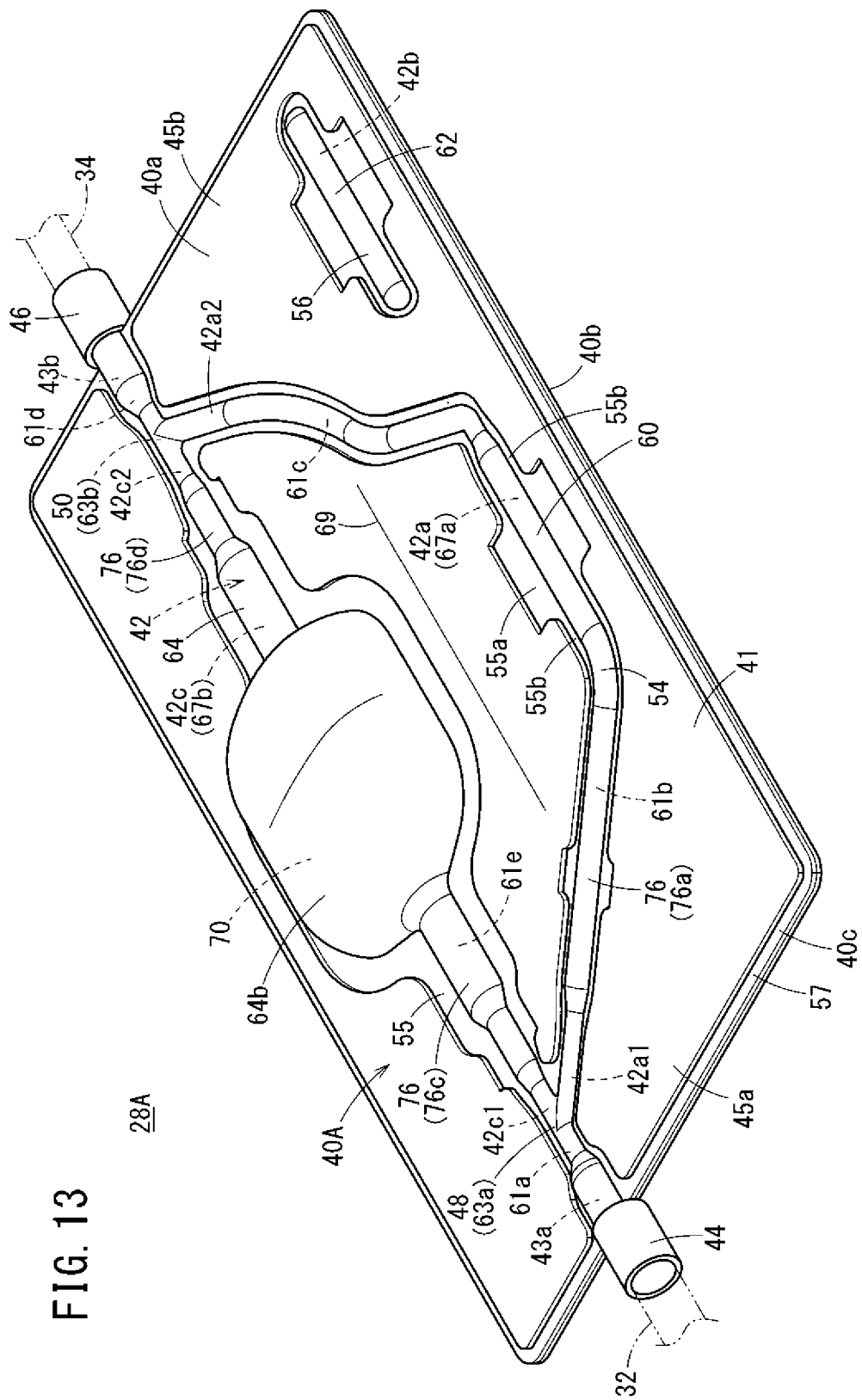
FIG. 13 is a perspective view of a blood component collection cassette according to another embodiment.

In the blood component collection system 10 described above, a blood component collection cassette 28A (hereinafter abbreviated to a "cassette 28A") illustrated in FIG. 13 may be adopted instead of the cassette 28. In a cassette body 40A of the cassette 28A, the second line 42b is a fluid non-communicating flow path independent of the first line 42a. Therefore, the second line 42b corresponds to a space independent of the first line 42a at all times, and air is enclosed in the second line 42b. A configuration of the other part of the cassette 28A is the same as a configuration of the cassette 28 illustrated in FIG. 2, etc. According to the blood component collection cassette 28A, the clamp 72b (FIG. 4) in the centrifugal separator 14 may not be used. Therefore, it is possible to simplify the configuration of the centrifugal separator 14, and to simplify control related to the operation of the clamp 72.

The present invention is not limited to the above-described embodiments, and can be variously modified within a range not departing from a subject matter of the present invention.

REFERENCE SIGNS LIST 10 blood component collection system
14 centrifugal separator
28, 28A blood component collection cassette
42 flow path
42a first line
42b second line
88 first load detector
90 second load detector

The invention claimed is:

1. A blood component collection cassette for use with a blood component separation device, the blood component collection cassette comprising:
 a cassette body having a sheet shape made of a soft material and including:
  a first flow path formed in the soft material for sending whole blood collected from a donor to the blood component separation device;
  a second flow path formed in the soft material for returning a predetermined blood component to the donor, wherein the first flow path and the second flow path are separate flow paths over a first section of the cassette body, wherein the first flow path and the second flow path overlap with one another in at least one second section of the cassette body, wherein the first flow path comprises a load detection soft portion located in the first section and made of the soft material for detecting internal pressure of the blood component collection cassette;
  a filter disposed in the second flow path, wherein the first flow path in the first section bypasses the filter,
 wherein the at least one second section of the cassette body, in which the first and second flow paths overlap, includes a first overlap part adjacent to a first edge of the cassette body and a second overlap part adjacent to a second edge of the cassette body opposite the first edge, and
 wherein the first section of the cassette body, in which the first and second flow paths are separate, extends between the first overlap part and the second overlap part;
 a first port member provided at the first edge of the cassette body and in fluid communication with the first overlap part, wherein the whole blood from the donor enters the cassette body through the first port member, and wherein the predetermined blood component exits the cassette body through the first port member; and
 a second port member provided at the second edge of the cassette body and in fluid communication with the second overlap part, wherein the whole blood from the donor exits the cassette body through the second port member, and wherein the predetermined blood component enters the cassette body through the second port member,
 wherein, in a plan view, the first overlap part is between the first port member and the filter along a first direction that extends from the first edge to the second edge of the cassette body, and
 wherein, in the plan view, the second overlap part is between the second port member and the filter along the first direction.

2. The blood component collection cassette according to claim 1, wherein
 the load detection soft portion corresponds to a pressure-receiving portion to be pressed by a first load detector of the blood component separation device in an attached state where the blood component collection cassette is attached to the blood component separation device.

3. The blood component collection cassette according to claim 1, wherein the cassette body is entirely made of the soft material.

4. The blood component collection cassette according to claim 2, wherein
 the blood component collection cassette includes:
  a cavity through which the whole blood and the predetermined blood component do not flow when the blood component separation device is in operation,
  wherein the pressure-receiving portion comprises a first pressure-receiving portion to be pressed by the first load detector, and
  wherein the cavity includes a second pressure-receiving portion made of the soft material to be pressed by a second load detector of the blood component separation device in the attached state, wherein the first pressure-receiving portion and the second pressure-receiving portion are located in the first section of the cassette body in which the first and second flow paths are separate.

5. The blood component collection cassette according to claim 4, wherein the cavity is in fluid communication with the first flow path in the first section via a coupling portion.

6. The blood component collection cassette according to claim 5, further comprising an action portion between the coupling portion and the second pressure-receiving portion on which a clamp acts.

7. The blood component collection cassette according to claim 1, wherein the first flow path separates from the second flow path at a branch portion, and
wherein the branch portion is configured such that a change in flow direction of a fluid in the branch portion occurs at an obtuse angle.

8. The blood component collection cassette according to claim 1, wherein the first flow path separates from the second flow path at a branch portion, and
wherein a flow path diameter of the branch portion is smaller than a flow path diameter of the first flow path and the second flow path immediately adjacent to the branch portion.

9. The blood component collection cassette according to claim 1, wherein the first flow path separates from the second flow path at a branch portion, and
wherein the branch portion comprises a protrusion partially protruding from an inner wall.

10. The blood component collection cassette according to claim 1, wherein the first port member and the second port member are provided at asymmetric positions with respect to each other.

11. The blood component collection cassette according to claim 2,
wherein the first flow path and the second flow path are parallel to one another over at least part of the first section, and
wherein a notch that penetrates the soft material of the cassette body in a thickness direction is provided between parallel portions of the first flow path and the second flow path.

12. The blood component collection cassette according to claim 2, wherein the cassette body comprises a first sheet and a second sheet made of the soft material,
wherein the first sheet and the second sheet are overlapped in a thickness direction and coupled to each other by welding,
wherein a seal portion corresponding to a welded area of the first and second sheets is formed along the first flow path and the second flow path, and
wherein a seal width of the seal portion formed on both sides of the pressure-receiving portion is larger than a seal width of the seal portion formed on both sides of the first flow path adjacent to the pressure-receiving portion.

13. The blood component collection cassette according to claim 1, further comprising:
a first branch point that splits the first overlap part into the first flow path and the second flow path,
a second branch point that splits the second overlap part into the first flow path and the second flow path.

14. The blood component collection cassette according to claim 7, wherein the obtuse angle is between 110 degrees and 135 degrees.

15. The blood component collection cassette according to claim 4, wherein said first pressure-receiving portion and said second pressure-receiving portion are in fluid communication on a linear fluid passage located in the first section of the cassette body.

16. The blood component collection cassette according to claim 15, wherein the first flow path separates from the second flow path at a branch portion, and
wherein the branch portion is configured such that a change in flow direction of a fluid in the branch portion occurs at an obtuse angle.

17. The blood component collection cassette according to claim 16, wherein a flow path diameter of the branch portion is smaller than a flow path diameter of the first flow path and the second flow path adjacent to the branch portion.

18. The blood component collection cassette according to claim 17, wherein the branch portion comprises a protrusion partially protruding from an inner wall.

19. The blood component collection cassette according to claim 16, wherein the obtuse angle is between 110 degrees and 135 degrees.

20. A blood component collection cassette for use with a blood component separation device having a first load detector, the blood component collection cassette comprising:
a cassette body having a sheet shape made of a soft material;
a plurality of fluid passages provided in the cassette body, the plurality of fluid passages including:
a first fluid passage formed in the soft material for sending whole blood collected from a donor to the blood component separation device; and
a second fluid passage formed in the soft material for returning a predetermined blood component to the donor, wherein the first fluid passage and the second fluid passage are separate from one another over a first section of the cassette body, wherein the first fluid passage and the second fluid passage overlap with one another in a first overlap section and a second overlap section of the cassette body, and wherein the first section of the cassette body includes a first part of the first fluid passage having a first pressure-receiving portion that is pressed by the first load detector to detect internal pressure of the blood component collection cassette in an attached state in which the blood component collection cassette is attached to the blood component separation device;
a first branch portion adjacent to a first edge of the cassette body and that splits the first overlap section into the first fluid passage and the second fluid passage;
a second branch portion adjacent to a second edge of the cassette body and that splits the second overlap section into the first fluid passage and the second fluid passage, wherein the first edge of the cassette body is opposite the second edge of the cassette body;
a third branch portion provided in the first fluid passage in the first section of the cassette body and that splits the first section of the cassette body into the first part of the first fluid passage and a second part of the first fluid passage;
a first port member disposed at the first edge of the cassette body and through which the whole blood from the donor enters the cassette body and the predetermined blood component exits the cassette body;
a second port member disposed at the second edge of the cassette body and through which the whole blood exits the cassette body and the predetermined blood component enters the cassette body; and
a filter disposed in the second fluid passage, wherein the first and second parts of the first fluid passage bypass the filter,
wherein the first part of the first fluid passage is connected between the first branch portion and the second branch portion, and
wherein the second part of the first fluid passage is connected to the third branch portion and terminates in the cassette body.

* * * * *